United States Patent [19]

Satzinger et al.

[11] Patent Number: 4,857,662
[45] Date of Patent: Aug. 15, 1989

[54] N-PHENYLBENZAMIDE DERIVATIVES

[75] Inventors: Gerhard Satzinger, Denzlingen; Manfred Hermann; Edgar Fritschi, both of St. Peter; Ute Weiershausen, Gundelfingen, all of Fed. Rep. of Germany

[73] Assignee: Gödecke Aktiengesellschaft, Berlin, Fed. Rep. of Germany

[21] Appl. No.: 578,466

[22] Filed: Feb. 9, 1984

[30] Foreign Application Priority Data

Feb. 19, 1983 [DE] Fed. Rep. of Germany ....... 3305755

[51] Int. Cl.$^4$ .................. C07C 103/82; A61K 31/165
[52] U.S. Cl. ..................................... 564/168; 514/619
[58] Field of Search ........................ 564/168; 514/619

[56] References Cited

U.S. PATENT DOCUMENTS 2,022,579 11/1935 Turski et al. ................... 564/168 X
3,488,388 1/1970 Altwicker et al. ............. 564/164 X
3,926,922 12/1975 Baron et al. ..................... 528/60 X

FOREIGN PATENT DOCUMENTS 21320 2/1982 Japan ................................ 564/164
1509035 7/1975 United Kingdom .

OTHER PUBLICATIONS

Dimitrijevic et al, CA 63:2808g (1965).
Smith et al, CA 64:11347d (1966).
Venkataraman, *The Analytical Chemistry of Synthetic Dyes*, p. 307 (1977).

*Primary Examiner*—Charles F. Warren
*Assistant Examiner*—Carolyn S. Greason
*Attorney, Agent, or Firm*—Ronald A. Daignault

[57] ABSTRACT

N-phenylbenzamide derivatives of the general formula I

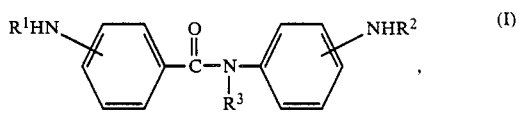

wherein the radicals $R^1$, $R^2$, and $R^3$, which can be the same or different, are a hydrogen atom or a methyl radical, as well as the pharmacologically acceptable salts thereof for controlling malignant, proliferative and auto-immune diseases and for immunosuppressive therapy upon grafting are described.

3 Claims, 2 Drawing Sheets

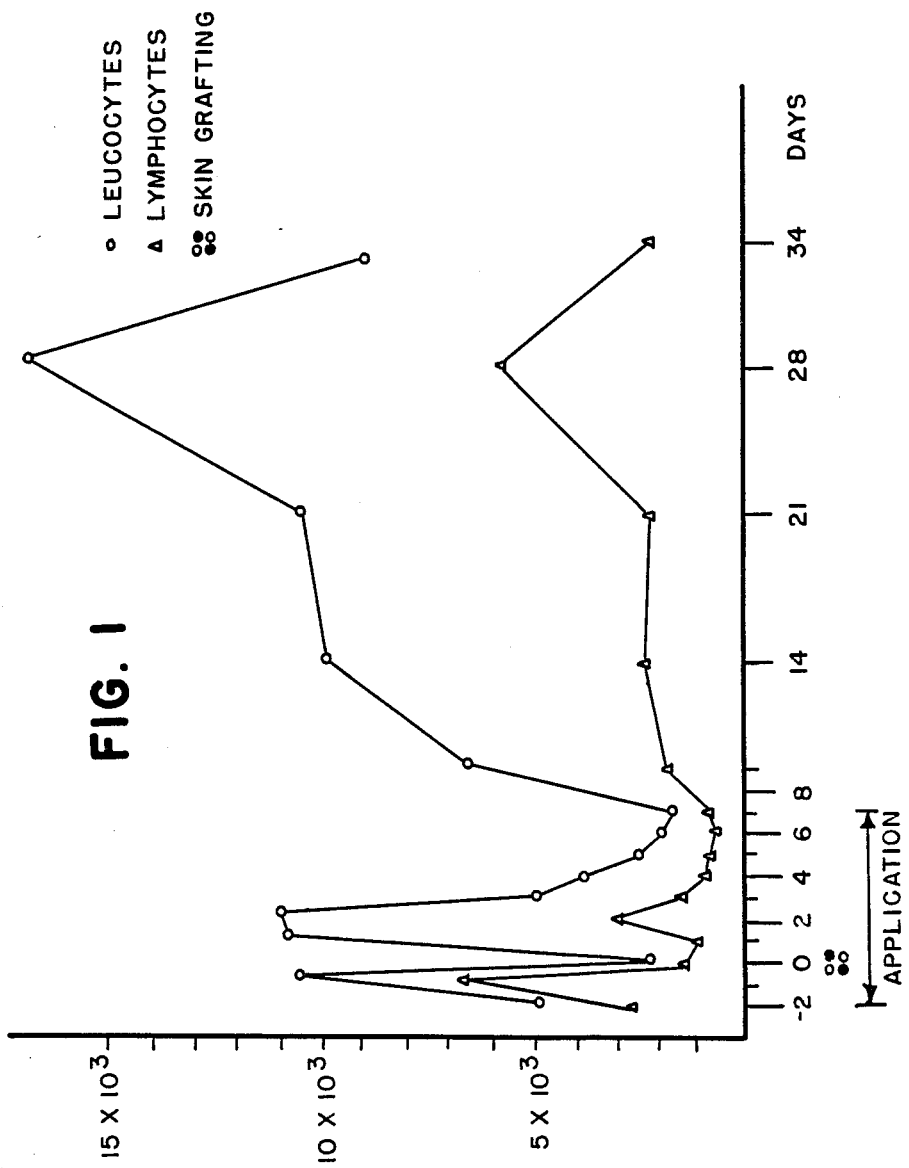

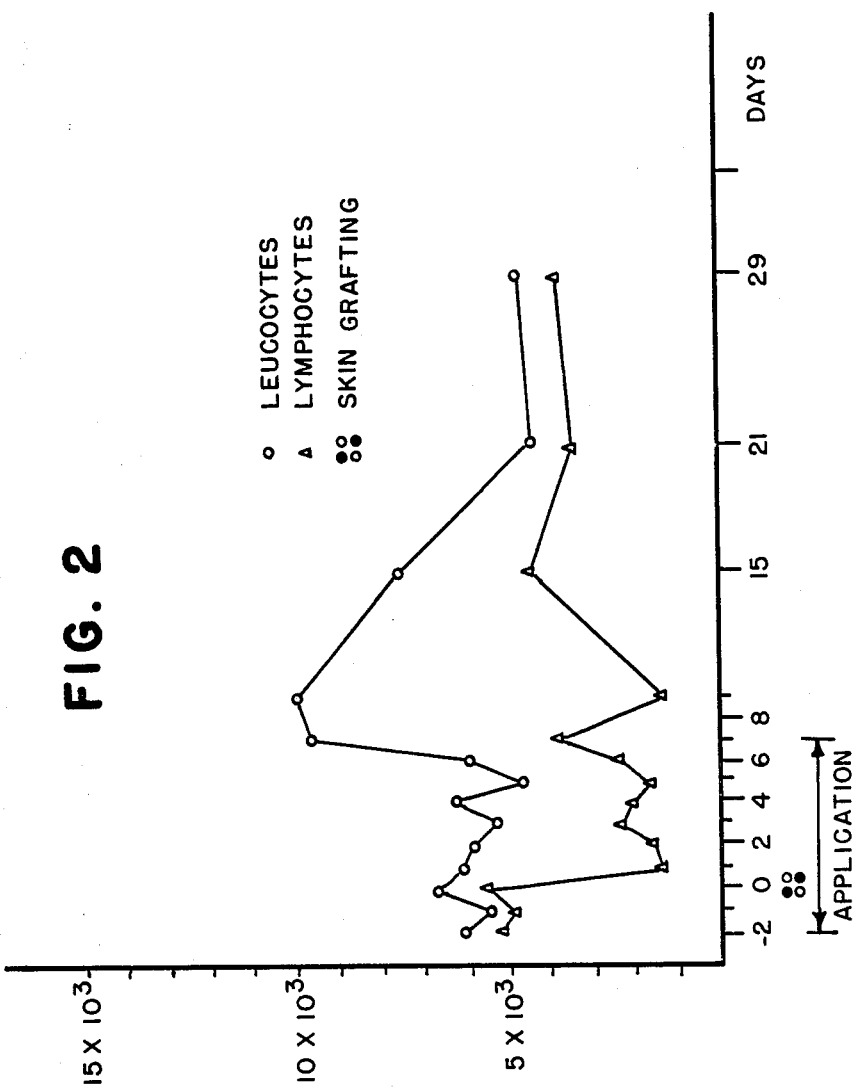

N-PHENYLBENZAMIDE DERIVATIVES

BACKGROUND OF THE INVENTION

Diaminobenzanilide derivatives have become known as starting products for the manufacture of polyurethane elastomers from U.S. Pat. No. 3,926,922. Nevertheless, no pharmacological properties have been described for this class of compounds.

SUMMARY OF THE INVENTION

The present invention relates to compounds of the general formula I

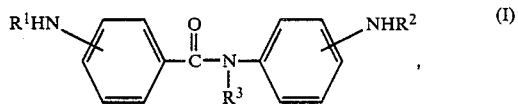

wherein the radicals $R^1$, $R^2$, and $R^3$, which can be the same or different, are a hydrogen atom or a methyl radical, as well as the pharmacologically acceptable acid addition salts thereof, possess interesting pharmacological properties, which make them suitable in particular for the treatment of malignant, proliferative and auto-immune diseases as well as for immunosuppressive therapy with transplantations.

Those compounds of the general formula I, wherein radicals $R^1$ and $R^2$ possess at least one methyl radical, are new compounds, which are characterized by the following general formula II:

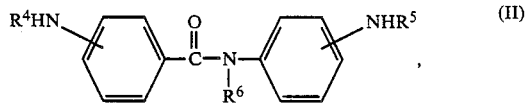

wherein at least one of the radicals $R^4$ and $R^5$ represents a methyl radical, and the remaining radicals $R^4$ to $R^6$, which can be the same or different, are a hydrogen atom or a methyl radical.

Thus, the present invention is concerned with new compounds of the general formula II, as well as with the application of compounds of the general formula I and pharmaceutical compositions thereof for the treatment of diseases of the immune system and for immunosuppressive therapy.

DETAILED DESCRIPTION

The compounds of the general formula II may be prepared by reacting, with one another in a previously known manner, compounds of the general formula IIIa and b:

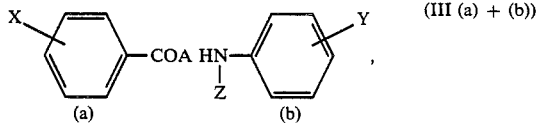

wherein A is a reactive acid group, Z a hydrogen atom or a methyl group and X and Y, which can be the same or different, are an amino group provided with a protective group or a nitro group, the compounds thus obtained of the general formula IV,

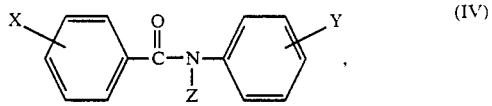

wherein X, Y, and Z have the aforementioned meanings, are reacted with hydrogen, and, if desired, subsequently converted by means of acids into the pharmacologically acceptable salts thereof.

Compounds of the general formulas I and II are particularly preferred, wherein the radicals —NH—$R^1$ and NH—$R^4$ are in para position to the carbonyl group.

The following individual substances are particularly preferred on the basis of their pharmacological action:
4-Amino-N-(2'-aminophenyl)-benzamide
4-methylamino-N-(2'-aminophenyl)-benzamide
4-amino-N-(2'-methylaminophenyl)-benzamide
4-amino-N-(2'-aminophenyl)-N-methyl-benzamide As salts, included are all therapeutically acceptable acid-addition salts, e.g. salts with hydrohalogenides, such as hydrochloric acid or hydrobromic acid, sulfuric acids, phosphoric acids, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid or pyruvic acid; phenylacetic acid, benzoic acid, p-aminopenzoic acid, anthranilic acid, p-hydroxybenzoic acid, salicylic acid or p-aminosalicylic acid, methanesulfonic acid, ethanesulfonic acid, hydroxyethanesulfonic acid, ethylenesulfonic acid; halogen benzenesulfonic acid, toluenesulfonic acid, naphthalenesulfonic acid, or sulfanilic acid; methionine, tryptophan, lysine or arginine.

The active substances according to the invention are advantageously administered in the form of a pharmaceutical preparation, which contains the active substances in free form or in the form of one of their therapeutically acceptable salts, mixed with pharmaceutical organic or inorganic solid or liquid carriers suitable, for example, for topical, enteral, e.g. oral or rectal, or above all, parenteral, such as IM or IV application. Those substances can be considered for the formation thereof which do not react with the new compounds, for example gelatine, lactose, starch, stearyl alcohol, magnesium stearate, talc, vegetable oils, benzyl alcohols, propylene glycols, vaseline or other pharmaceutical carriers.

The pharmaceutical preparations can be in the form of e.g. tablets, sugar-coated tablets, capsules, suppositories, ointments, creams or in liquid form as solutions, suspensions or emulsions. If necessary, they are sterilized and/or contain adjuvants such as preserving, stabilizing, wetting or emulsifying agents, solutes or salts to change the osmotic pressure or buffers. They can also contain further active substances.

The dosage to be applied depends on the clinical picture of the disease to be treated and on individual factors.

Doses of 10 to 300 mg, in particular 20 to 100 mg are generally administered. The individual dosage can also exceed this in special cases.

The compounds according to formula IIIa are reacted with compounds of formula IIIb in a previously known manner. Particularly acid halogenides, acid anhydrides or acid imidazolides or ester groups are used as reactive acid groups A, these permitting a reaction with the amino group. Thus, A denotes preferably halogen, imidazolyl, acyl or lower alkanoyl groups.

The usual groups which are also found in peptide chemistry, e.g. the acetyl, the benzyloxy or the carbobenzoxy group may be used as protective groups for X and/or Y.

The reaction with hydrogen using suitable catalysts (platinum or palladium) is conducted in such a manner that on the one hand the free nitro groups are reduced to primary amino groups and, on the other hand, the protective groups attached to the amino groups are split off hydrogenolytically. In this manner one arrives at the methyl-substituted or unsubstituted amino groups $R^1$—NH—, $R^2$—NH— or $R^4$—NH—, and $R^5$—NH—, as desired. An acetyl group being used as protective group is split off hydrolytically e.g. with hydrochloric acid.

The substances according to the invention possess surprising pharmacological activities and are in particular agents for immunosuppression/immunoregulation in skin, organ and bone marrow transplantations, for immunosuppression/immunoregulation in disturbances of the cellular and humoral immune system (e.g. autoaggression diseases, immuno-complex diseases, diseases of rheumatic typology), for topical and/or systemic treatment of malignant neoplasia (including those of the hematopoietic system, the skin, CNS) and for the topical and/or systemic treatment of benign proliferative diseases (e.g. psoriasis). On the basis of the proven cytostatic action an antiviral action is also taken into consideration.

The compounds of the general formula I can be distinguished from the known cytostatic and immunosuppressive agents particularly on account of their lipophilia, inherent in their chemical structure, by their potency, their topical activity and the controlability of their action and side-effects due to special kinetics of action.

Contrary to most substances, which cannot pass the blood-drain barrier due to their hydrophilic properties and therefore do not allow a satisfactory therapeutical influence e.g. on malignant tumors of the CNS, the substances according to the invention reach the CNS as a consequence of their favoring distribution coefficient (log $V_K$ of example 1=2.2, n-octanol/water pH 7.4/20° C.). This is also the case with intragastric application, as shown by certain pharmacological effects.

The passing of the blood-brain barrier has opened up new avenues previously unknown for influencing therapeutically proliferative as well as auto-immune processes in the CNS. With a lipophilic cytostatic agent there is still the possibility of enrichment in particularly high-fat tumors, whereby a more efficient medicinal influence on such neoplasms can be achieved.

Comparison investigations of the substances according to the invention against the immunosuppressive standard azathioprine demonstrate the formers' superiority: to obtain approximately the same effect on the survival time of allogeneic skin grafts in rats, 300% to 700% higher doses are necessary in the case of azathioprine compared to the compounds of formula I.

No report has yet been presented for traditional cytostatic agents on a topical antiproliferative activity, as can be demonstrated for the substances according to the invention.

Furthermore, it was found that the suppressive action on peripheral leukocytes and lymphocytes in rhesus monkeys is quickly reversible upon discontinuing one of the substances according to the invention. No comparable short-term extensive reattainment of normal hematological findings can be observed with the conventional cytostatics and immunosuppressive agents (e.g. cyclophosphamide, methotrexate, azathioprine). It can be concluded from this that overdoses arising from individually varying responses and the resulting side-effects are better to control than with conventional cytostatics and immunosuppressive agents.

Steroids, azathioprine, antilymphocyte globulin (ALG), antithymocyte globulin (ATG) and cyclosporine A are used in immunosuppression. The side-effects of these therapies are considerable, and the complications dangerous. The compounds of the present invention demonstrate a particular lack of side-effect and purely for this reason alone represent great therapeutic progress.

The current psoriasis medication has to be designated as extraordinarily unsatisfactory. Corticoids are amongst the most effective antipsoriatic agents. Systemically, however, they have to be administered in such high doses that steroid toxicity frequently occurs. After their discontinuation severe relapses or even transformations into the chronic pustular forms can occur. Relapses also occur following topical application of corticoids.

The folic-acid antagonist methotrexate is likewise regarded as effective antipsoriatic agent. Methotrexate is an effective agent with medium to severe psoriasis-arthritis. On account of the high risk of hepatotoxicity, myelotoxicity and gastrointestinal toxicity, the methotrexate treatment is, however, restricted to patients acutely ill with generalized severe forms of psoriasis. The compounds of this application have a proliferation-inhibiting effect even with topical application, with the result that apart from the systemic treatment of psoriasis-arthritis they can also gain importance for the topical treatment of psoriatic skin abnormalities. Side-effects along the lines of those found with the antipsoriatic agents already on sale, are not anticipated with the substances according to the invention on the basis of their chemical properties.

Great importance must be placed on the development of lipophilic cytostatic agents, since the wellknown substances do not reach the CNS at all or reach the CNS only in therapeutically insufficient concentrations, and thus a satisfactory cytostatic medication of malignant tumors of the CNS is currently not possible. The different types of leukemia in particular come into consideration as an especially interesting indication for a lipophilic cytostatic agent, since these frequently disseminate into the CNS, from whence the disease process is further sustained. Another potential advantage of a cytostatic agent with lipophilic properties is the enrichment in particularly high-fat tumors, which can therefore possibly be influenced preferably.

The following comparison trials verify the action of the compounds of the general formula I.

COMPARISON TRIALS

I. Investigation for immunosuppressive activity in the skin graft survival test in rats Substance A (4-amino-N(2'-aminophenyl)-benzamide) according to the invention was tested on rats and rhesus monkeys for immunosuppressive activity in the skin grafting model; in the experiments on rats it was compared with the international immunosuppressive standard azathioprine as well as with a combination medication generally used at present in organ transplantations, consisting of high-dosage azathioprine and low-dosage methylprednisolone. Substance A was at least equally as effective as the comparison medication in these trials, although far smaller substance quantities were used. In rhesus monkeys the immunosuppressive action was also markedly clear. As demonstrated on this species, the extension of the normal survival time of allogeneic skin grafts affected by substance A is characterized by the simultaneous distinct reduction of the peripheral lymphocytes.

(A) Technique

Comparison medication:
Trial I/azathioprine + methylprednisolone
Trial II/azathioprine
Preparation: As suspension freshly prepared before each adminstration
Route of administration: intragastric via stomach tube, suspended in 0.8% Methocel
Volume: 0.01 ml per gram body weight and dose Dosage schedule:
Trial I/from Day −3 before grafting to Day +6
Trial II/from Day −2 before grafting to Day +9
Tested doses:
Trial I/10 mg/kg over 6 days, afterwards 5 mg/kg daily for 4 days
Trial II/4–8 mg/kg daily increasing over 12 days (B) Trial Design Two allogeneic skin grafts from a donor rat are transferred to a receiving rat from an unrelated inbred strain. The panniculus carnosus attached to the graft may either be removed by dissection (suprapannicular graft) or be left on the graft (subpannicular graft). Grafting is conducted on Day 0 under light ether narcosis subsequent to shaving and cleanup of the grafting sites. The grafts are fixed on the graft receptor sites by dressing with a suitable bandage. From Day +9 a protective collar is placed on the animals, the bandage removed and the status of the grafts daily controlled. The assessment of the graft function is conducted by means of a graduation scale, which allows for a differentation of rejection corresponding to a three-degree of severity score. The trial ends on the day when 50% of the animals of one group have rejected both grafts. The lengthening of the graft survival time in comparison to the controls is determined in days.

(C) Results

As can be deduced from the following Table I and II, in Trial I substance A was superior to an immunosuppressive standard medication comprising azathioprine and methylprednisolone. In Trial II substance A was equally as effective as the immunosuppressive standard azathioprine. Due to the high activity of substance A, however, far smaller quantities of the substance were necessary to achieve the action compared with the standard medication.

Table I shows the results of Trial I, skin graft survival test, in rats. Recipient: Long Evans ♂, Donor: Lewis ♂ Two suprapannicular grafts were transferred from a donor to a recipient.

Table II shows the results of Trial II, skin graft survival test, in rats. Recipient: Osborne Mendel ♂, Donor: Lewis ♂ Two suprapannicular grafts were transferred from a donor to a recipient.

TABLE I

| Test Substance Dosage | Animals with Two Rejected Grafts/n (%) | | | | | | | | |
|---|---|---|---|---|---|---|---|---|---|
| | Day +9 | Day +10 | Day +11 | Day +12 | Day +13 | Day +14 | Day +15 | Day +16 | Day +17 |
| Control Methocel i.g. | 1/6(17) | 3/6(50)* | 4/6(66) | 4/6(66) | 4/6(66) | 5/6(83) | 6/6(100) | — | — |
| Substance A** 10 mg/kg i.g. from Day −3 to Day +2 afterwards 5 mg/kg i.g. from Day +3 to Day +6 | 0/5(0) | 0/5(0) | 0/5(0) | 0/5(0) | 1/5(20) | 1/5(20) | 3/5(60)* | 4/5(80) | 5/5(100) |
| Azathioprine 40 mg/kg i.g. + methylprednisolone 2 mg/kg i.g. from Day −3 to Day −6 | 0/6(0) | 0/6(0) | 1/6(17) | 2/6(33) | 2/6(33) | 4/6(66)* | 6/6(100) | — | — |

*Day of rejection: at least 50% of the animals have rejected both grafts.
**Substance A: 4-amino-N—(2′-aminophenyl)-benzamide (Example 1).

TABLE II

| Test Susbstance Dosage | Animals with Two Rejected Grafts/n (%) | | | | |
|---|---|---|---|---|---|
| | Day +8 | Day +9 | Day +10 | Day +11 | Day +12 |
| Control Methocel i.g. | 2/10(20) | 5/10(50)* | 6/10(60) | 8/10(80) | 9/10(90) |
| Substance A** 4–8 mg/kg i.g. from Day −2 to Day +9 | 0/10(0) | 1/10(10) | 1/10(10) | 1/10(10) | 6/10(60)* |
| Azathioprine 20–60 mg/kg i.g. from Day −2 to | 0/10(0) | 1/10(10) | 2/10(20) | 4/10(40) | 5/10(50)* |

TABLE II-continued

| Test Susbstance Dosage | Animals with Two Rejected Grafts/n (%) | | | | |
|---|---|---|---|---|---|
| | Day +8 | Day +9 | Day +10 | Day +11 | Day +12 |
| Day +9 | | | | | |

*Day of rejection: at least 50% of the animals have rejected both grafts.
**Substance A: 4-amino-N—(2'-aminophenyl)-benzamide (Example 1).

II. Investigation of Substance A for immunosuppressive activity in the skin graft survival test in rhesus monkeys (Macaca mulatta)

The demonstration of the action in the skin grafting model is to be evaluated as evidence of an inhibition of the cellular immune system (T-lymphocytes), since this is decisively involved in the rejection of allogeneic grafts according to the currently prevalent opinion.

An inhibition of the humoral immune system (antibody-producing B-lymphocytes) by the substances of the invention and a possibility of therapy resulting from this, e.g. for autoaggression diseases, which are characterized by an increase in antibody production against the body's own tissues, can currently only be concluded indirectly. An increased susceptibility to bacterial infections observed in rats treated over a sustained period with high doses of substance A is to be regarded as an indirect demonstration of the inhibition of humoral immunoresistance.

| (A) Technique | |
|---|---|
| Control standard: | Not used for ethical reasons |
| Preparation: | Freshly prepared before each administration |
| Route of administration: | Intragastric via stomach tube, suspended in 0.8% Methocel |
| Dosage schedule | 1 × daily for 10 days |
| Tested dose: | 10 mg/kg |

(B) Trial Design

Altogether four allogeneic skin grafts from two different donor animals are transferred crosswise to one unrelated receiving animal. At first the grafts are removed under ketamine narcosis from the shaven and cleaned stomach skin of the donor animals and freed of any fat attached. The four graft receptor sites are prepared on the shaven and cleaned back of the receiving animal under ketamine narcosis by removing suitably-sized pieces of skin. Subsequent to successful hemostasis, the grafts are spread out on the graft receptor sites and sewn to the edges of the wound. The wound is covered with a suitable dressing material and this is fixed with an elastic bandage. The bandage is opened on the 5th, 7th, and 9th day after grafting and the function of the grafts examined. On the 9th day the bandage is no longer replaced. The graft function is then controlled daily until rejection has occurred.

(C) Results

Controls are dispensed with in this trial on primates for ethical reasons. Comparisons are drawn with the normal survival of allogeneic skin grafts or historic controls, stated as ten days. A lengthening of the normal graft survival time could be achieved with substance A in the tested dosage on test animal ZE by six to seven days, and by four to five days on test animal YL. This result is to be interpreted as a distinct immunosuppressive action of the substance according to the invention.

FIGS. 1 and 2 demonstrate the influence of a ten-day medication of Substance A on leukocytes and lymphocytes in the plasma of rhesus monkeys.
Dosage: 1 × daily 10 mg/kg i.g.
FIG. 1: Rhesus monkey ZE, ♀
FIG. 2: Rhesus monkey YL, ♀

III. Investigation of the antineoplastic activity of Substance A on three tumor models in mice Upon intragastric administration of substance A to tumor-carrying mice, these demonstrated a significant increase in the average survival time and a distinct retardation in the growth of the tumor concerned in comparison to the untreated control animals, according to the tumor model used.

| (A) Technique | |
|---|---|
| Preparation: | As suspension freshly prepared before each administration |
| Route of administration: | oral, suspended in 0.8% Methocel |
| Volume: | 0.01 per gram body weight and dose |
| Dosage schedule | daily for 9 days, if not otherwise stated |
| Tested doses: | 60, 120, 180, 240 mg/kg daily |

(B) Tumor Description

L 1210/Rij adaption of L1210 leukemia in $CD_2$ mice (C57B1×DBA2, F1 hybride). On the day before administration of the substance $10^5$ leukemic cells are inoculated intraperitoneally. The cages are controlled 2× daily for dead animals. The terminal point is the mean survival of five mice/dosage compared with ten untreated controls.

Osteosarcoma. C22LR in BCBA mice (C57B1×CBA/Rij, F1 hybride). The tumor is subcutaneously inoculated bilaterally into the sides. It is measured at least 2× weekly in three dimensions. The terminal point is the retardation of growth. It is defined as the difference of the average time in which the volume of five to ten tumors in five treated animals reaches a given value in comparison with that of five to ten tumors in the control animals. This value was determined as four times that of the average volume at commencement of treatment.

Lewis Lung Tumor in BCBA mice. The procedure is the same as with osteosarcoma. The volume of the tumor was determined here at 800 mm$^3$ (=product of the diameters in three dimensions).

(C) Results

Due to the toxicity of the selected dosages, daily applications were not possible in most of the dosage groups. After mortality had occurred in all groups following two or more applications of 120 mg/kg or more, the number of administrations to the surviving animals was reduced. The findings can be seen in the following Tables III to V.

Assessment: The tested dosages were too high. In spite of this a significant activity of the tested substance could be proved with L1210 in a moderate dosage, a good activity with osteosarcoma and a moderate activity with Lewis Lung Tumor.

The following Tables III to V reveal the results of the testing of substance A on neoplastic activity in mice.

TABLE III

L1210

| Dosage | | Mean Survival Time (Days) | % Increase in Mean Survival Time |
|---|---|---|---|
| Controls | (n = 10) | 8 | — |
| Test groups: | | | |
| 9 × 60 mg/kg PO | (n = 5) | 11 | 38% |
| 7 × 120 mg/kg PO | (n = 5) | 6 | toxic death |
| 4 × 180 mg/kg PO | (n = 5) | 5 | toxic death |
| 4 × 240 mg/kg PO | (n = 5) | 5 | toxic death |

TABLE IV

Osteosarcoma

| Dosage | | Surviving Animals | Retardation in Growth of Tumor (Days) |
|---|---|---|---|
| Controls | (n = 5) | 5/5 | — |
| Test groups: | | | |
| 9 × 60 mg/kg ip | (n = 5) | 5/5 | 7,8 (p = 0,0001) |
| 4 × 120 mg/kg PO | (n = 5) | 0/5(Day 5) | toxic death |
| 2 × 180 mg/kg PO | (n = 5) | 1/5 | 9,6 |
| 1 × 240 mg/kg PO | (n = 5) | 5/5 | 3,1 (p = 0,001) |

TABLE V

Lewis Lung Tumor

| Dosage | | Surviving Animals | Retardation in Growth of Tumor (Days) |
|---|---|---|---|
| Controls | (n = 5) | 5/5 | — |
| Test groups: | | | |
| 9 × 60 mg/kg ip | (n = 5) | 5/5 | 3,8 (p = 0,061) |
| 4 × 120 mg/kg PO | (n = 5) | 0/5 | toxic death |
| 2 × 108 mg/kg PO | (n = 5) | 0/5 | toxic death |
| 1 × 240 mg/kg PO | (n = 5) | 5/5 | 3,5 (p = 0,018) |

IV. Investigation of substance A for antiproliferative activity upon topical administration to rats (A) Technique

| Control standard: | No control standard known |
|---|---|
| Preparation: | Fresh before each administration |
| Route of administration: | Topically by pipetting as 0.5% solution in absolute ethanol |
| Volume: | 1 ml per animal and dose |
| Tested dose: | 5 mg/animal daily for 14 days 10 mg/animal daily for 7 days |

(B) Trial Design

A protective collar is placed on male rats of the long Evans strain, fur color "blackhooded." A rectangle measuring 3 cm long and 1.5 cm wide is marked with the aid of a template on the dorsal skin in the region of the black dorsal hair strip subsequent to shaving and cleansing. The test solution is slowly applied dropwise to this rectangle, so as to avoid it running off onto the surrounding skin. The solvent is applied in the same manner to the control animals. After 21 days of treatment the hair growth is assessed on the treated areas compared with the control areas.

(C) Results

A clear inhibition of hair growth can be seen with the treated animals in comparison with the control animals.

Assessment: Although it cannot be excluded that part of the substance administered was involved in a systemic manner in the inhibition of the growing hair follicle due to a possible percutaneous resorption, it could be demonstrated that a distinct antiproliferate action is achieved with the substance of the invention on adnexes of the skin, upon topical application.

V. Central Actions of Substance A

The penetrating ability of the substances of the invention into the CNS and other lipoid organs can also be demonstrated by their marked anticonvulsive effects in the maximal electroconvulsion test (Swinyard et al., J. Pharm. exp. Ther. 106, 319 (1952) and in the pentetrazoleconvulsion model (loc. cit.):

TABLE VI

Anticonvulsive Action of Substance A in Mice

| Convulsion model | Substance A $ED_{50}$ mg/kg (i.g.) | Diphenylhydantoin $ED_{50}$ mg/kg (i.g.) |
|---|---|---|
| Electro-convulsion | 30.0 (21–42) | 22.5 (18–28) |
| Pentetrazole-convulsion | 44.0 (32–60) | 9.5 (7–13) |

So as to make the magnitude of the central effects clear, the standard antiepileptic agent diphenylhydantoin was brought in as a reference substance.

The seven-day values of the acute, oral (i.g.) toxicity of substance A and diphenylhydantoin in mice are listed comparatively in Table VII.

TABLE VII

| | $LD_{50}$ mg/kg | Confidence level in mg/kg | |
|---|---|---|---|
| | | lower | p = 0.05 upper |
| Substance A | 625 | 469.9 | 831.2 |
| Diphenyl-hydantoin | 128 | 114.2 | 143.3 |

The following Examples are given for the purpose of illustrating the invention:

EXAMPLE 1

4-Amino-N-(2'-aminophenyl)-benzamide $C_{13}H_{13}N_3O$ MG 227.26

22.7 g o-Nitroaniline, dissolved in 130 ml anhydrous dioxane, are mixed dropwise with a solution of 30.4 g p-nitrobenzoylchloride in 150 ml dry dioxane. The reaction is brought to a close by heating for one hour under reflux. Upon cooling to 15° C. N-(2'-nitrophenyl)-4-nitrobenzamide is precipitated in crystalline form. After recrystallizing from chlorobenzene 39 g (83% of theory) with a melting point of 217°–218° C. are obtained.

39 g of the dinitro-product are hydrated in 550 ml dimethylformamide in the presence of 10 g Raney-Ni for one hour at 25° C. and a pressure of above 2 atmospheres.

It is filtered off from the catalyst, the solvent removed in a vacuum and the title product recrystallized from ethanol. Yield 20.2 g (66% of theory) with a melting point of 180°–181° C.

Using a solution of HCl-gas in ethanol the compound can be converted to dihydrochloride, which is 4% water soluble.

4-Amino-N-(2′aminophenyl)-benzamide-dihydrochloride $C_{13}H_{15}N_3Cl_2O$ MG 300.18, melting point 340° C. (from ethanol)

EXAMPLE 2

4-Methylamino-N-(2′-aminophenyl)-N-benzamide 2.71 g N-(2-Nitrophenyl)-4-methylamino-benzamide are dissolved in 300 ml tetrahydrofuran and hydrated with Raney-Ni in a shaking apparatus. The temperature rises from 21° C. to 26° C. during hydration. Subsequent to filtering off from the catalyst, the clear solution is evaporated and the residue recrystallized from ethyl acetate.

There is obtained 1.3 g (56.5 % of theory) of 4-Methylamino-N-(2′-aminophenyl)-N-benzamide, mp.189° C.

The N-(2-nitrophenyl)-4-methylamino-benzamide employed as starting product is prepared in the following manner:

4.535 g (0. 03 mol) 4-Methylamino-benzoic acid are heated while stirring with 9.19 g (0.09 mol) acetic anhydride to 100° C. for one hour. The crystals precipitated out after cooling of the clear solution are filtered off with suction and washed with ethyl acetate (mp. 199°–201° C.). The N-acetyl-4-methylamino-benzoic acid obtained (yield 62 %) is then converted by means of thionylchloride in dioxane into the acid chloride. The excess of thionyl chloride is then stripped off with some dioxane in a water-jet vacuum. 2.76 g (0.02 mol) o-nitroaniline in 10 ml dry dioxane are added dropwise to the reaction mixture and the solution mixed with 4.04 g (0.04 mol) triethyl amine (as HCl-absorber). The reaction mixture is then boiled under reflux for one hour. The evaporated reaction residue is mixed with 40 ml of water and extracted with methylene chloride. After evaporation of the organic phase, 4 ml isopropanol are added thereto and the crystals formed filtered off by suction after previous stirring for 30 minutes.

There are obtained 5.1 g N-(2-Nitrophenyl)-4-N-acetyl-N-methyl)-amino-benzamide (mp. 162° C.) in a yield of 55.6 % of theory. The crude product thus obtained is then suspended in a small amount of ethanol and hydrolyzed with the seven-fold molar amount of concentrated hydrochloric acid under reflux for 9 hours. The reaction mixture is evaporated to dryness and brought to crystallization by the addition of isopropanol, then dissolved in 40 ml water and alkalized with ammonia. After extraction with methylene-chloride there are obtained 1.4 g N-(2-nitrophenyl)-4-methylamino-benzamide with a mp. of 187° C. and in a yield of 51 % of theory.

The following compounds are obtained in an analogous manner:

4-amino-N-(2′-methylaminophenyl)-N-benzamide
4-methylamino-N-(2′-methylaminophenyl)-N-benzamide

EXAMPLE 3

4-Amino-N-(2′-aminophenyl)-N-methylbenzamide 22.82 g (0.15 mol) N-methyl-o-nitroaniline are dissolved in 70 ml dry tetrahydrofuran and mixed dropwise with 30.6 g (0.165 mol) p-nitrobenzoyl chloride in 90 ml dry tetrahydrofuran while stirr ng and bubbling nitrogen through the reaction mixture. Stirring is then continued under reflux for two hours under an atmosphere of nitrogen. The reaction mixture obtained is concentrated and recrystallized from acetyl acetate.

There are obtained 29.2 g (64.6 % of theory) of N-methyl-N-(2-nitrophenyl)-4-nitrobenzamide with a flow point of 137°–138° C., which is dissolved in 800 ml tetrahydrofuran and hydrated with 10 g Raney-Ni in a shaking apparatus while applying cooling with water. The temperature should not exceed an upper limit of 25° C. After 7 hours, 10 g Raney-Ni are again added thereto and after further 6 hours the colorless solution evaporated to dryness, the residue dissolved in ethyl acetate and precipitated with diisopropyl ether.

There are obtained 18 g of 4-Amino-N-(2′-aminophenyl)-N-methyl-benzamide; mp. 159°–160° C.

The following compounds are obtained in an analogous manner:

4-methylamino-N-(2′-aminophenyl)-N-methylbenzamide
4-methylamino-N-(2′-methylaminophenyl)-N-methylbenzamide
4-amino-N-(2′-methylaminophenyl)-N-methylbenzamide

We claim:
1. A compound of the formula

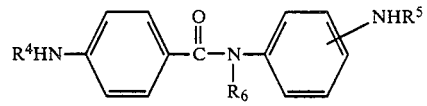

wherein one of the radicals $R^4$ and $R^5$ represents methyl and the other hydrogen; $R^6$ is hydrogen or methyl, or a pharmacologically acceptable acid addition salt thereof.

2. A compound and being 4-methylamino-N-(2′-aminophenyl)-benzamide.

3. A compound and being 4-amino-N-(2′-methylaminophenyl)-benzamide.

* * * * *